US010596204B2

(12) United States Patent
Cardinault

(10) Patent No.: US 10,596,204 B2
(45) Date of Patent: Mar. 24, 2020

(54) USE OF PROPOLIS FOR COMBATING PATHOLOGICAL CONDITIONS ASSOCIATED WITH OBESITY

(71) Applicant: POLLENERGIE, Saint-Hilaire-de-Lusignan (FR)

(72) Inventor: Nicolas Cardinault, Agen (FR)

(73) Assignee: POLLENERGIE, Saint Hilaire de Lusignan (FR)

( * ) Notice: Subject to any disclaimer, the term of this patent is extended or adjusted under 35 U.S.C. 154(b) by 369 days.

(21) Appl. No.: 14/897,978

(22) PCT Filed: Jun. 11, 2014

(86) PCT No.: PCT/FR2014/051408
§ 371 (c)(1),
(2) Date: Dec. 11, 2015

(87) PCT Pub. No.: WO2014/199077
PCT Pub. Date: Dec. 18, 2014

(65) Prior Publication Data
US 2016/0143959 A1 May 26, 2016

(30) Foreign Application Priority Data
Jun. 11, 2013 (FR) ...................... 13 55357

(51) Int. Cl.
*A61K 35/644* (2015.01)
*A61K 36/28* (2006.01)
*A61K 36/185* (2006.01)
*A61K 36/48* (2006.01)
*A23L 33/105* (2016.01)
*A23L 21/20* (2016.01)
*A61K 9/14* (2006.01)
*A61K 31/05* (2006.01)

(52) U.S. Cl.
CPC ............ *A61K 35/644* (2013.01); *A23L 21/20* (2016.08); *A23L 33/105* (2016.08); *A61K 9/14* (2013.01); *A61K 31/05* (2013.01); *A61K 36/185* (2013.01); *A61K 36/28* (2013.01); *A61K 36/48* (2013.01)

(58) Field of Classification Search
None
See application file for complete search history.

(56) References Cited

U.S. PATENT DOCUMENTS 5,922,324 A * 7/1999 Aga ...................... A61K 31/192
424/439
2013/0288959 A1 * 10/2013 Imai ...................... A61K 38/45
514/6.7

FOREIGN PATENT DOCUMENTS

| CN | 101700324 | 5/2010 |
|---|---|---|
| CN | 101828660 | 9/2010 |
| CN | 102380051 | 3/2012 |
| JP | 2004-43375 | 2/2004 |
| JP | 2006-28174 | 2/2006 |
| JP | 2008-50301 | 3/2008 |
| KR | 20080012457 | 2/2008 |

OTHER PUBLICATIONS

Aoi et al. (2013) Biochemical and Biophysical Research Communications 432: 650-653. (Year: 2013).*
Bahadoran et al. (2013) Journal of Diabetes and Metabolic Disorders, 12:43, 9 pages (Year: 2013).*
Delaprane et al. (2012) Journal of Nutritional Biochemistry, 23, 557-566. (Year: 2012).*
Fuliang et al. (2005) Pharmacological Research 51: 147-152 (Year: 2005).*
Iio et al. (2010) Phytomedicine 17: 974-979. (Year: 2010).*
Kumazawa et al. (2004) Food Chemistry 84: 329-339. (Year: 2004).*
Kurek-Gorecka et al. (2014) Molecules, 19, 78-101. (Year: 2014).*
Szkudelska et al. (2010) European Journal of Pharmacology, 635: 1-8. (Year: 2010).*
Ueda et al. (2013) Intern. Union of Biochem. and Molec. Biol. vol. 39, No. 4, 457-466. (Year: 2013).*
Volpi et al. (2004) Electrophoresis, 25, 1872-1878. (Year: 2004).*
Teixeira et al. (2008) eCAM 2010: 7(3): 307-315. (Year: 2008).*
Kitamura et al. (2013) Adipocyte, 2:4, 227-236. (Year: 2013).*
Zhu et al. (2011) Evidence-Based Complementary and Alternative Medicine, vol. 2011, Article ID 468529, 8 pages (Year: 2011).*
McCune et al. (2005) Flavonoids, xanthones and the antioxidant polyphenols. In: Traditional Herbal Medicines for Modern Times. vol. 6, Issue: Antidiabetic Plants. pp. 293-303 (Year: 2005).*
Orsolic et al. (2008) Recent Progress in Medicinal Plants, vol. 22: 443-540. (Year: 2008).*
Bankova et al. (2005) Recent trends and important developments in propolis research. eCAM 2005 2(1): 29-32 (Year: 2005).*
Matsuhige et al. (1996) Phytomedicine vol. III (2): pp. 203-209. (Year: 1996).*
Raskin et al. (2004) Current Pharmaceutical Design, 10: 3419-3429. (Year: 2004).*
Revilla et al. (1998) J. Agric. Food Chem. 46: 4592-4597. (Year: 1998).*
Ristivojevic et al. (2015) Nat. Prod. Comm. vol. 10 (No. 11): 1869-1876. (Year: 2015).*
Szkudelski et al. (2015) Biochimica et. Biophysica Acta. 1852: 1145-1154. (Year: 2015).*
Aoi et al., "Improvement of insulin resistance, blood pressure and interstitial pH in early developmental stage of insulin resistance in OLETF rats by intake of propolis extracts," Biochemical and Biophysical Research Communications, vol. 132, pp. 650-653, 2013.

(Continued)

*Primary Examiner* — Russell G Fiebig
(74) *Attorney, Agent, or Firm* — Young & Thompson

(57) ABSTRACT

The use of propolis or an extract of propolis as a food supplement for preventing and/or combating pathological conditions associated with diet-induced obesity, and in particular type II diabetes, and a specific a composition suitable for this use.

7 Claims, No Drawings

(56) References Cited

OTHER PUBLICATIONS

Choi et al., "Artepilln C, as a PPARγ ligand, enhances adipocyte differentiation and glucose uptake in 3T3-L1 cells," Biochemical Pharmacology, vol. 81, pp. 925-933, 2011.
Database WPI, Week 201034, Thomson Scientific, London, GB; AN 2010-F21040.
Iio et al., "Ethanolic extracts of Brazilian red propolis promote adipocyte differentiation through PPARγ activation," Phytomedicine, vol. 17, pp. 974-979, 2010.
Juman et al., "Caffeic Acid Phenethyl Ester Suppresses the Production of Pro-inflammatory Cytokines in Hypertrophic Adipocytes through Lipopolysaccahride-Stimulated Macrophages," Bio. Pharm. Bull., vol. 35, No. 11, pp. 1941-1945, 2012.
Koya-Miyata et al., "Propolis Prevents Diet-Induced Hyperlipidemia and Mitigates Weight Gain in Diet-Induced Obesity in Mice," Bio. Pharm. Bull., vol. 32, No. 12, pp. 2022-2028, 2009.
Li et al., "Effects of Encapsulated Propolis on Blood Glycemic Control, Lipid Metabolism, and Insulin Resistance in Type 2 Diabetes Mellitus Rats," Evidence-Based Complementary and Alternative Medicine, vol. 2012, pp. 1-8.
Nagaoka et al., "Caffeic Acid Phenethyl Ester (CAPE) Analogues: Potent Nitric Oxide Inhibitors from the Netherland propolis," Bio. Pharm. Bull., vol. 26, No. 4, pp. 487-491, 2003.

\* cited by examiner

USE OF PROPOLIS FOR COMBATING PATHOLOGICAL CONDITIONS ASSOCIATED WITH OBESITY

FIELD OF THE INVENTION

This invention relates to the use of propolis as a food supplement for combating pathological conditions associated with obesity and in particular type 2 diabetes. In our current societies, the prevalence of obesity and type 2 diabetes is growing and of major concern.

BACKGROUND OF THE INVENTION

Defined as an abnormal or excessive accumulation of body fat, obesity can have significant repercussions on the health of individuals. It is strongly associated with the appearance of disorders, in particular insulin resistance originating from type 2 diabetes.

Type 2 diabetes is a chronic illness due to an inadequate secretion of insulin for producing the expected physiological effect that, associated with obesity and a sedentary lifestyle, leads to a series of complications such as retinopathies, neuropathies, renal failures, and cardiovascular diseases.

The essential cause of obesity is an energy imbalance between calories consumed and those expended. For treatment, it is therefore advised, of course, to change one's lifestyle, in particular to adopt a diet that is less rich in fat and sugars and to engage in physical activity. This first approach is supplemented by sometimes aggressive pharmacological and medical treatments that can go so far as surgical intervention.

BRIEF SUMMARY OF THE INVENTION

The objective of this invention is to propose a nutritional approach of natural origin whose purpose is to limit the onset of pathological conditions associated with diet-induced obesity, in particular type 2 diabetes.

For this purpose, the invention has as its object the use of propolis or a propolis extract for preventing and/or combating obesity and/or type 2 diabetes. Actually, surprisingly enough, the administration of propolis makes it possible to limit and/or to combat the onset of disorders associated with weight gain and obesity.

In particular, the purpose of the invention is the use of a composition that comprises at least one propolis extract that contains polyphenols as a food supplement for preventing and/or limiting obesity and/or type 2 diabetes.

The invention also relates to a particular composition that is suitable for this use.

Propolis is a product that is produced by bees from resinous, gummy, and balsamic substances, collected on the buds of certain trees and shrubs, with which they incorporate salivary secretions therein.

Surprisingly enough, according to the invention, propolis has good effectiveness for preventing and/or combating pathological conditions associated with diet-induced obesity, in particular type 2 diabetes.

Advantageously, the administration to an obese person and/or a type-2-diabetic person of a composition that comprises at least one propolis extract makes it possible to control and to limit the onset of disorders associated with obesity, such as silent inflammation and insulin resistance.

DETAILED DESCRIPTION OF THE INVENTION

The invention is now described in detail.

The object of the invention is therefore a composition that comprises at least one propolis extract for its application as a food supplement for preventing and/or combating the pathological conditions associated with obesity, in particular type 2 diabetes.

In terms of the invention, food supplement is defined as a food product whose object is to complete the normal diet and that constitutes a concentrated source of nutrients and/or other substances that have a nutritional or physiological effect, by themselves or combined.

Propolis extract is defined as any collected propolis that is transformed by an extraction process that makes it possible to remove the impurities that are present in the crude extract and/or to concentrate the propolis in one or more of its components.

The propolis extract can come in any form. Preferably, it comes in the form of a powder.

The useful propolis extract according to the invention contains polyphenols; in particular, it comprises at least 20% polyphenols by weight of dry material of the extract.

The propolis that is used can be of any identified botanical origin. It can be of multiple botanical origins if they are well-identified and characterized.

Very preferably, these are poplar propolis and/or *Baccharis* propolis (Brazilian green propolis) and/or *Dalbergia ecastaphyllum* propolis (red). The *Baccharis* propolis can be a *Baccharis Dracunculifolia* propolis.

When the propolis extract is a poplar propolis extract, it preferably comprises at least 30% polyphenols by weight of dry material of the extract.

The extract that is present in the composition can be obtained by a process that comprises the following stages:
  Extraction of propolis,
  Concentration.

The extract can then be reconcentrated and finally transformed.

The different stages of the process should be carried out without destroying the active ingredients and without using solvents.

According to a particularly suitable embodiment, the extract that is used according to the invention can be obtained by a process that comprises the following stages:
  Maceration of crude propolis in an alcohol solution, and
  Concentration by evaporation.

The extract can then be transformed into powder.

The propolis extract that is obtained is incorporated into a composition.

The composition that comprises the propolis extract is used as a food supplement.

The composition comprises at least one propolis extract, but can contain multiple extracts, in particular two or three extracts of different botanical origins.

Preferably, the composition comprises at least one extract that is selected from among:
  A poplar propolis extract,
  A *Baccharis propolis* extract (Brazilian green propolis),
  A *Dalbergia ecastaphyllum* propolis extract (red).

According to a suitable embodiment, the composition contains a mixture of two of these propolis extracts, or a mixture of three propolis extracts.

The composition according to the invention, in addition to the propolis extract(s), can contain at least one plant extract. Preferably, it comprises a *Trigonella foenum-graecum* extract and/or a *Moringa oleifera* extract.

The composition can also contain resveratrol, starting from a synthetic form or a plant extract.

The composition can also contain excipients known by one skilled in the art, such as kaolin or Fibregum® or other texturing, coating and/or gastro-resistant agents.

According to a suitable embodiment, the composition comes in the form of a powder.

The composition according to the invention, involving a food supplement, is administered in addition to meals. It can be administered in various galenical forms, in particular in the form of a capsule or tablet.

In a preferred manner, the daily dose of composition comprises between 400 and 1,000 mg of propolis extract by weight of dry material. Preferably, the daily dose is divided into 2 or 3 servings.

The composition according to the invention that comprises at least one propolis extract is used for its application as a food supplement for preventing and/or combating the pathological conditions associated with obesity, in particular type 2 diabetes.

In addition to insulin resistance or type 2 diabetes, among the other pathological conditions associated with diabetes for which the food supplement according to the invention can be used, it is possible to cite in particular metabolic inflammation or silent inflammation and arteriosclerosis.

The use according to the invention makes it possible to act in particular on the main molecules secreted by adipose tissue during interprandial periods, in particular on:
 Free fatty acids,
 Adiponectin,
 Leptin,
 Inflammatory cytokines, and/or
 Chemokines.

The free fatty acids are normally secreted by adipose tissue during interprandial periods. In the course of obesity, when the adipose tissue begins to become insulin-resistant, in part because of the hypertrophy and the hyperplasia of the adipose tissue that becomes hypotoxic, lipolysis is accelerated, leading to the massive release of free fatty acids into circulation. The latter will, in the area of the liver and muscles, disrupt the action of insulin.

According to the invention, propolis can be used for limiting the release of free fatty acids into circulation.

Adiponectin, synthesized primarily by the adipocytes, circulates at high concentrations in thin individuals (5 to 30 mg/l of plasma). Adiponectin increases sensitivity to insulin, affects the production of glucose on the hepatic level by inhibiting the expression of two enzymes essential to neoglucogenesis, and also has anti-inflammatory properties by modulating the expression of pro/anti-inflammatory cytokines, in particular that of TNF-$\alpha$. In contrast to other adipokines, its production and its secretion are reduced in obese individuals that have an insulin resistance or type 2 diabetes.

According to the invention, propolis can be used for increasing the adiponectin level in obese individuals having an insulin resistance or type 2 diabetes.

Like adiponectin, leptin is produced primarily by adipocytes. Its plasmatic concentration as well as its expression in adipose tissue are positively correlated with the severity of the obesity.

According to the invention, propolis can be used to regulate the leptin level in obese individuals.

Inflammatory cytokines, such as TNF-$\alpha$, are cytokines that are synthesized by numerous tissues including obese adipose tissue and that, in addition to their well-known pro-inflammatory activities, are involved in the pathogenesis of insulin resistance.

Advantageously, it is known that propolis is capable of inhibiting pro-inflammatory factors such as TNF-$\alpha$.

Finally, the chemokines are chemoattractant molecules in particular for macrophages, secreted by the adipocytes.

The use according to the invention makes it possible to limit the chemokine level in particular of the MCP-1 ("monocyte chemotactic protein-1"), key factor in the recruitment of macrophages in adipocytic tissue and MIP-1$\alpha$ (macrophage inflammatory protein-1$\alpha$).

Advantageously, in particular owing to its different actions, the composition according to the invention makes it possible to prevent and/or combat obesity and/or the associated pathological conditions, in particular type 2 diabetes.

The invention is now illustrated by examples of extracts and compositions.

EXAMPLES OF PROPOLIS EXTRACTS

The propolis that is used, in particular poplar propolis, can be obtained by implementing the technique of grids, which makes it possible to obtain propolis with particular characteristics suitable for medical use in comparison to propolis obtained by the scraping technique. The grid method makes it possible to obtain propolis with a higher polyphenol level and a reduced percentage of wax.

Once the propolis is collected, it is treated by implementing an extraction process comprising the following stages:
 Propolis is mixed in an extractor with alcohol according to a ratio of 1/2.5 to 1/5 (w/v) for a given time period,
 The mixture then undergoes filtration so as to keep in liquid solution only the active ingredients of propolis: polyphenols,
 A final clarification by gravitational decanting can optionally be carried out if necessary.

This process makes possible the development of a liquid extract that is concentrated in terms of active ingredients.

This liquid extract can then optionally also be concentrated in terms of active ingredients by alcoholization. A soft extract that is very concentrated in terms of propolis active ingredients is then obtained. This soft extract can be transformed into powder.

Example of Extract 1

An example of a propolis extract obtained by implementing this process is a poplar propolis extract in powder form, having at least 30% total polyphenols by weight of dry material.

Among the polyphenols, the extract comprises in particular:
 At least 8% ($\pm$0.8%) pinocembrine
 At least 5% ($\pm$0.5%) chrysin
 At least 4% ($\pm$0.4%) galangin, and
 At least 1.8% ($\pm$0.18%) CAPE,
with the percentages being given by weight of dry material relative to the total polyphenols that are present in the extract.

Example of Extract 2

An example of propolis extract that is obtained by implementing this process is a *Baccharis* propolis extract in powder form, having at least 20% total polyphenols by weight of dry material.

The extract comprises in particular at least 10% ($\pm$1%) artepellin C by weight of dry material relative to the total polyphenols that are present in the extract.

Example of Extract 3

An example of propolis extract that is obtained by implementing this process is a red propolis extract in powder form. The extract comprises in particular isoflavonoids.

EXAMPLES OF COMPOSITIONS

Example of Composition 1

A useful composition example according to the invention comprises:
- 50 to 75% of a propolis extract according to Example 1, 2 or 3
- 5 to 15% Fibregum
- 10 to 15% silica
- 10 to 15% kaolin

Example of Composition 2

A useful composition example according to the invention comprises:
- 15 to 50% Brazilian green propolis extract (Example 2)
- 15 to 50% poplar propolis extract (Example 1)
- 10 to 30% Fibregum
- 10 to 30% silica
- 10 to 30% kaolin

Example of Composition 3

A useful composition example according to the invention comprises:
- 10 to 50% red propolis extract (Example 3),
- 10 to 50% Brazilian green propolis extract (Example 2),
- 10 to 50% poplar propolis extract (Example 1) that comprises at least 30% polyphenols,
- 10 to 30% Fibregum,
- 10 to 30% silica,
- 10 to 30% kaolin.

The invention claimed is:

1. A method for treating type II diabetes associated with diet-induced obesity comprising administering to a subject in need thereof an effective amount of a composition comprising at least one poplar propolis extract that comprises 25%-35% polyphenols by weight of dry material,
wherein the extract comprises in particular
at least 8% (±0.8%) pinocembrine,
at least 5% (±0.5%) chrysin,
at least 4% (±0.4%) galangin, and
at least 1.8% (±0.18%) CAPE,
with the percentages being given by weight of dry material relative to the total polyphenols that are present in the extract; and
wherein the daily dose of the composition comprises between 400 and 1000 mg of propolis extract by weight of dry material.

2. The method according to claim 1, wherein the composition further comprises at least one plant extract.

3. The method according to claim 1, wherein the composition further comprises resveratrol in a synthetic form or a plant extract.

4. The method according to claim 1, wherein the composition is a powder.

5. The method according to claim 1, wherein the composition is a food supplement that is administered in addition to meals.

6. The method according to claim 1, wherein the composition further comprises an additional propolis extract selected from the group consisting of *Baccharis* propolis extract and *Dalbergia ecastaphyllum* propolis extract.

7. The method according to claim 1, wherein the composition further comprises *Baccharis* propolis extract and *Dalbergia ecastaphyllum* propolis extract.

* * * * *